US009161557B2

(12) United States Patent
Ishii et al.

(10) Patent No.: US 9,161,557 B2
(45) Date of Patent: Oct. 20, 2015

(54) DRY COMPOSITION FOR ORAL INGESTION AND GEL COMPOSITION PREPARED JUST BEFORE USE FOR ORAL INGESTION

(75) Inventors: Kazumi Ishii, Tokyo (JP); Saichi Ono, Tokyo (JP); Tadahiko Chiba, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 1137 days.

(21) Appl. No.: 11/628,744

(22) PCT Filed: May 23, 2005

(86) PCT No.: PCT/JP2005/009354
§ 371 (c)(1),
(2), (4) Date: Dec. 7, 2006

(87) PCT Pub. No.: WO2005/120458
PCT Pub. Date: Dec. 22, 2005

(65) Prior Publication Data
US 2009/0269328 A1    Oct. 29, 2009

(30) Foreign Application Priority Data
Jun. 7, 2004  (JP) .................................. 2004-168368

(51) Int. Cl.
| A61K 9/14 | (2006.01) |
| A61K 47/32 | (2006.01) |
| A61K 47/36 | (2006.01) |
| A61K 47/38 | (2006.01) |
| A61K 33/44 | (2006.01) |
| A23L 1/03 | (2006.01) |
| A61K 8/04 | (2006.01) |
| A23K 1/16 | (2006.01) |
| A23K 1/18 | (2006.01) |
| A23L 1/0522 | (2006.01) |
| A23L 1/053 | (2006.01) |
| A61K 9/46 | (2006.01) |
| A61K 9/06 | (2006.01) |

(52) U.S. Cl.
CPC ............. *A23L 1/0305* (2013.01); *A23K 1/1643* (2013.01); *A23K 1/1846* (2013.01); *A23L 1/053* (2013.01); *A23L 1/0522* (2013.01); *A61K 8/042* (2013.01); *A61K 9/0007* (2013.01); *A61K 9/06* (2013.01); *A61K 9/14* (2013.01); *A61K 9/141* (2013.01); *A61K 9/146* (2013.01)

(58) Field of Classification Search
CPC ........... A61K 9/146; A61K 9/14; A61K 9/06; A61K 9/042
See application file for complete search history.

(56) References Cited

U.S. PATENT DOCUMENTS

| 3,418,999 | A | * | 12/1968 | Davis ............................ 604/514 |
| 4,465,517 | A | * | 8/1984 | Shields .......................... 106/35 |
| 4,681,764 | A | | 7/1987 | Endo et al. |
| 4,761,284 | A | * | 8/1988 | Nishimura .................... 424/125 |
| 5,292,518 | A | | 3/1994 | Kuhrts |
| 5,427,799 | A | * | 6/1995 | Valentine et al. ............. 424/451 |
| 5,552,462 | A | * | 9/1996 | Yeh ................................. 524/55 |
| 5,916,789 | A | | 6/1999 | Webbers et al. |
| 6,299,867 | B1 | | 10/2001 | Aoyagi et al. |
| 6,375,977 | B1 | * | 4/2002 | Auguste et al. .............. 424/447 |
| 6,589,507 | B1 | | 7/2003 | Bauer |
| 2001/0055619 | A1 | * | 12/2001 | Petereit et al. ............... 424/490 |
| 2002/0025911 | A1 | | 2/2002 | Aoyagi et al. |
| 2002/0176540 | A1 | | 11/2002 | Sakaida |
| 2004/0082777 | A1 | * | 4/2004 | Kamada et al. ................ 536/95 |

FOREIGN PATENT DOCUMENTS

| DE | 198 59 231 | 6/2000 |
| JP | 06-022761 | 2/1994 |
| JP | 07-184483 | 7/1995 |
| JP | 09-075723 | 7/1995 |
| JP | 10-131819 | 5/1998 |
| JP | 11-322606 | 11/1999 |
| JP | 2000-103730 | 4/2000 |
| JP | 2000-291419 | 9/2000 |
| JP | 2000-318096 | 11/2000 |
| JP | 2002-104997 | 4/2002 |
| JP | 2002-308786 | 10/2002 |
| JP | 3522708 | 2/2004 |
| JP | 2005-314415 | 11/2005 |
| JP | 2005-314416 | 11/2005 |
| WO | WO 98/03260 | 7/1996 |
| WO | WO 98/03259 | 12/1996 |
| WO | 00/06122 | 7/1999 |

OTHER PUBLICATIONS

Thombre, Advanced Drug Delivery Reviews, 2004, 56, 1399-1413.*
Duvallet et al., Polymer Bulletin, 1989, 21, 517-521.*
International Search Report for PCT/JP2005/009354, dated Jun. 28, 2005.
Chinese Patent Office Office Action dated Sep. 19, 2008, first page in Chinese with English translation.
Extended European Search Report for corresponding Application No. EP 05 74 1450, dated May 25, 2010.
International Search Report. 2005.
Abstracts in the Annual meeting of The Pharmaceutical Society of Japan, 1993, vol. 113, No. 4, p. 264 (13-03).

* cited by examiner

*Primary Examiner* — Abigail Fisher
(74) *Attorney, Agent, or Firm* — Birch, Stewart, Kolasch & Birch, LLP

(57) ABSTRACT

A dry composition for oral ingestion characterized by comprising as an active ingredient a gas-releasing substance which releases gas by soak with water, and further comprising a gel base in an amount sufficient for gel formation; a gel composition for oral ingestion formed by adding water or a liquid diluent to the dry compound when taking; and a mixed feed obtainable by mixing the gel composition with a feed, are disclosed.

6 Claims, 1 Drawing Sheet

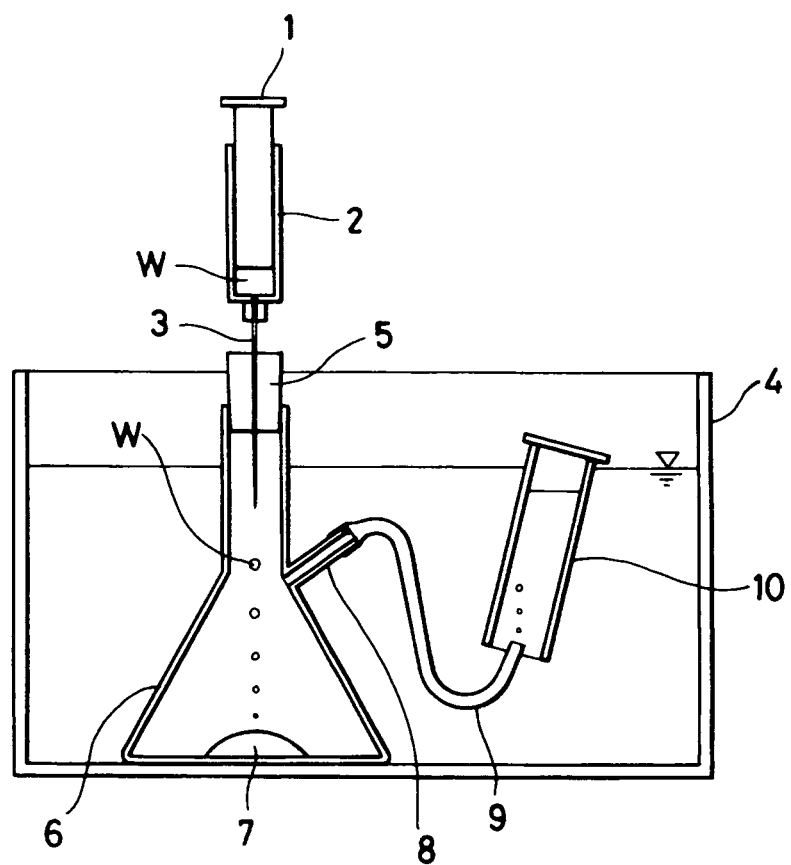

DRY COMPOSITION FOR ORAL INGESTION AND GEL COMPOSITION PREPARED JUST BEFORE USE FOR ORAL INGESTION

TECHNICAL FIELD

The present invention relates to a dry composition for oral ingestion and a gel composition prepared just before use for oral ingestion. The dry composition for oral ingestion can be converted to a gel (or a jelly) at room temperature in a very short time, at most, approximately one minute, only by mixing water or a liquid diluent therewith, without heating or cooling, and a gel composition for oral ingestion capable of being easily taken by even a person having a difficulty when swallowing can be obtained.

BACKGROUND ART

Recently, not only a maintenance of the effectiveness, safety, and quality of drugs, but also an alleviation of the burden on patients during oral ingestion, has been demanded in the medical sense. This is because there is an increasing trend in the number of patients having a difficulty when taking food (for example, a person with dentures, a person unable to properly chew, or a patient suffering from dysphagia) due to the progressive aging of society, and there is a growing number of patients having a difficulty when taking medicaments by oral administration.

Formulations for oral administration are commonly provided, for example, as solutions, capsules, granules, pills, powders, tablets, or syrups. The definitions of these formulations are described in the Japanese Pharmacopoeia. When a person having a difficulty when swallowing takes such a formulation together with water, a formulation such as powders or granules sometimes exists in the oral cavity, or a formulation such as tablets, pills, or capsules can sometimes cause choking when taken by the person.

To resolve these disadvantages, various pharmaceutical compositions have been proposed. For example, an agent which enables an easy swallowing is known (patent reference 1). According to this agent, a medicament may be formulated with a gel base and a sugar alcohol and, immediately before taking, may be mixed with water or an appropriate liquid substance, to rapidly form a gel (or a jelly) without heating or cooling. According to the disclosures of patent reference 1, when a water-soluble gelatin is used as the gel base, a hard-jelly formulation ideal for an agent which enables an easy swallowing may be obtained, but a gelation time thereof is approximately 45 minutes. Patent reference 1 also discloses that a hard-jelly formulation may be obtained within 1 minute, without heating or cooling, by using a combination of water-soluble gelatin (a gel base) and erythritol (a sugar alcohol). In general, heating or cooling is required to obtain a hard jel by using a gel base. Therefore, it is practically useful to obtain such a hard jel at room temperature in a short time, as disclosed in patent reference 1. However, since sugar alcohols have a high hygroscopicity and are easily liquefied, the combinations thereof with medicaments in which the stability is lost by humidity are limited. Particularly, in the case of the spherical adsorbing carbons described below, an adsorption capacity is decreased while in contact with water, and thus, combinations of the spherical adsorbing carbons and sugar alcohols are inappropriate.

Further, a use of a gel base to enable an easy taking of medicaments, together with a masked agent in which a bad taste (for example, bitterness, astringency, or acidity) of medicaments is alleviated by masking, is known (patent reference 2). Patent reference 2 also discloses that a rapid gelation by only adding water at room temperature without heating or cooling is important, and discloses examples in which a masked bitter antimicrobial agent was used together with a gel base, by using a gelation caused by crosslinking of alginate and a polyvalent metal ion. However, a gelation time of each example was several minutes, and a gelation in a short time was not attained. Further, an agent used together with the gel base was a masked agent which masked bad tastes, and it was not proposed as a general purpose technique.

Furthermore, a use of a gel base for improving difficulty of deglutition of specific antitumor agents is known (patent reference 3). The object of the technique described in patent reference 3 is to provide a jelly formulation capable of enabling an easy taking of a mixing agent of tegafur and uracil as an antitumor agent, for a patient suffering from dysphagia or an intraoral disorder caused as a side effect of the mixing agent. The formulation is provided as a lyophilized product obtained by preparing a jelled gel with a gel base and lyophilizing the jelled gel. Although, when the lyophilized product is returned to a jelled gel formulation by adding water thereto, the jelled gel formulation may be obtained in a short time at room temperature without heating or cooling, it is generally necessary to perform a heating or cooling treatment when preparing the lyophilized product, and it sometimes takes a long time to carry out these treatments. Further, facilities for preparing the lyophilized product are necessary, and that leads to higher costs. Furthermore, in the case of the spherical adsorbing carbons described below, when such a lyophilized product, which is obtained by preparing a jelled gel with a gel base and lyophilizing the jelled gel, is returned to a jelled gel formulation by adding water thereto, when taking, a gel formulation cannot be prepared in a short time because a gas-releasing property of the spherical adsorbing carbons is lost.

An adsorbent for internal use capable of being orally administered and alleviating functional disorders of kidneys or the liver has been developed and is in use (patent reference 4). The adsorbent for internal use consists of a porous carbonaceous substance having specific functional groups (i.e., a modified spherical activated carbon); is very safe and stable to a body; and has a useful selective adsorbability, that is, an excellent adsorbability of harmful substances in the presence of a bile acid in the intestine, and a low adsorbability of useful substances such as digestive enzymes in the intestine. Further, the adsorbent for internal use is widely and clinically used for a patient suffering from a disorder of a liver or renal function, as an oral medicament having few side effects such as constipation. The adsorbent disclosed in patent reference 4 is manufactured by preparing spherical activated carbons from pitches such as petroleum pitch as a carbon source, and subjecting the spherical activated carbons to an oxidation treatment and a reduction treatment. Further, an adsorbent for oral administration in which the above selective adsorbability (i.e., an excellent adsorbability of harmful substances and a low adsorbability of useful substances in the intestine) is improved is known (patent reference 5). The adsorbent for oral administration disclosed in patent reference 5 is based on the findings that the selective adsorbability is improved when a volume of pores having a pore diameter of 20 to 15000 nm is 0.04 mL/g or more and less than 0.10 mL/g, and thus, can effectively adsorb harmful substances, and is extremely useful for diseases in which a suppression of the adsorbability of useful substances in the intestine is desired.

The adsorbent for internal use is generally provided in the form of fine granules or capsules. Since a dose is relatively large, it was desirable to improve the ease of taking. For example, when taking fine granules, some patients dislike a feeling of any residual in the oral cavity. Further, many patients feel repulsion and pain when taking relatively large medicaments such as capsules, and further, many patients cannot take granules or capsules without taking in a large quantity of water.

Further, for patients suffering from a renal disease or renal failure, an amount of water to take is limited, and such patients are required to take minimal water when ingesting granules or capsules. Therefore, patients who essentially need a large quantity of water when taking granules or capsules feel intense pain when doing so.

[Patent Reference 1] Japanese Unexamined Patent Publication (Kokai) No. 2002-104997

[Patent Reference 2] Japanese Unexamined Patent Publication (Kokai) No. 2000-103730

[Patent Reference 3] Japanese Unexamined Patent Publication (Kokai) No. 11-322606

[Patent Reference 4] Japanese Examined Patent Publication (Kokoku) No. 62-11611

[Patent Reference 5] Japanese Patent No. 3522708

DISCLOSURE OF THE INVENTION

Problems to be Solved by the Invention

The present inventors engaged in intensive research to facilitate taking the above adsorbent for internal use. For example, a jelly to aid swallowing, containing agar as a main component, is known. When the jelly for aiding swallowing was mixed with the above adsorbent for internal use, and administered, the present inventors discovered that the adsorbing ability was declined. Further, the process for mixing the jelly in a form of gel with the granular adsorbent required special skills, and time to uniformalize the mixture.

The present inventors engaged in intensive research, and focused on the facts that the adsorbent for internal use has a gas-releasing property and vigorously generates many microbubbles in water. When the adsorbent for internal use was put into water, gas was released in a gel base, and the present inventors found that a gel aggregate providing a sufficient ease of taking was formed in an extremely short time at room temperature, without heating or cooling and special skills.

Further, it was found that the gel composition containing the adsorbent for internal use not only improved taking for humans, but also facilitated taking for animals, particularly pet animals. As shown in Examples described below, there was a problem in that, when the adsorbent for internal use was mixed, in the form of a solid, with a dried food, and the mixture fed to a cat, the adsorbent was separated from the dried food, and almost all of the adsorbent and a part of the dried food were left. In contrast, when the gel composition containing the adsorbent for internal use was mixed with the dried food, the adsorbent was attached to the surface of the dried food, and the adsorbent was ingested together with the dried food. As a result, all of the mixed feed was completely ingested.

The present invention is based on the above findings.

Means for Solving the Problems

The present invention relates to a dry composition for oral ingestion, characterized by comprising as an active ingredient a gas-releasing substance which releases gas by soak with water, and further comprising a gel base in an amount sufficient for gel formation.

According to a preferred embodiment of the dry composition of the present invention, the gel base is one or more substances selected from the group consisting of acacia gum, propylene glycol alginate, a starch, carageenan, karaya gum, carboxyvinyl polymers, sodium carboxymethyl starch, xanthan gum, guar gum, cellulose derivatives and salts thereof, tara gum, tragacanth, and locust bean gum.

According to another preferred embodiment of the dry composition of the present invention, the gel base is a gel-forming high molecular weight compound with a molecular weight of 10,000 or more.

According to still another preferred embodiment of the dry composition of the present invention, the gas-releasing substance is a substance which releases gas and absorbs water by soak with water.

According to still another preferred embodiment of the dry composition of the present invention, the gas-releasing substance is an adsorbent for internal use.

According to still another preferred embodiment of the dry composition of the present invention, the adsorbent for internal use is a spherical adsorbing carbon.

According to still another preferred embodiment of the dry composition of the present invention, an amount of the gel base is 0.1 to 100 parts by weight with respect to 100 parts by weight of the gas-releasing substance.

The present invention relates to a gel composition for oral ingestion, characterized by being formed by adding water or a liquid diluent to the dry compound when taken for oral ingestion.

According to a preferred embodiment of the gel composition of the present invention, an amount of the water or liquid diluent is 100 to 10,000 parts by weight with respect to 100 parts by weight of the composition for oral ingestion.

The gel composition for oral ingestion may be used by mixing a feed therewith. The present invention relates to a mixed feed obtainable by mixing the gel composition for oral ingestion with a feed.

According to a preferred embodiment of the mixed feed of the present invention, the feed is a dried food.

According to another preferred embodiment of the mixed feed of the present invention, the feed is a feed for an animal other than a human.

EFFECTS OF THE INVENTION

The dry composition for oral ingestion of the present invention can be converted to a gel (or a jelly) at room temperature in a very short time, at most, approximately one minute, only by mixing water or a liquid diluent therewith, without heating or cooling. The obtained gel composition for oral ingestion can be easily taken by a person having a difficulty when swallowing.

Further, the obtained gel composition for oral ingestion can be easily swallowed as an aggregate without manducating, or as aggregates divided by biting the aggregate several times, in a similar fashion as when eating jelly sweets. The gel composition for oral ingestion prepared in a vessel can be recovered by using a spoon or the like, as one aggregate.

When the gel composition containing the adsorbent for internal use is mixed with a feed (particularly a dried food), the adsorbent can be easily ingested to an animal other than a human, together with the feed.

BRIEF DESCRIPTION OF THE DRAWINGS

[FIG. 1]

FIG. 1 schematically illustrates an apparatus for measuring an amount of gas released from a spherical carbonaceous adsorbent.

EXPLANATIONS OF REFERENCE SIGNS IN DRAWINGS

1 . . . piston; 2 . . . cylinder; 3 . . . needle; 4 . . . water tank; 5 . . . rubber plug; 6 . . . side arm flask; 7 . . . spherical carbonaceous adsorbent; 8 . . . side arm; 9 . . . tube; 10 . . . graduated cylinder; W . . . water.

BEST MODE FOR CARRYING OUT THE INVENTION

The dry compound for oral ingestion of the present invention will be explained hereinafter.

The gas-releasing substance used in the compound of the present invention is a substance which releases gas by soak with water at room temperature (20° C.), particularly a porous substance. Since gas contained in pores of the gas-releasing porous substance is released by substituting water or a liquid diluent therefor, the gas released from the porous substance is generally air. An amount of the gas (particularly air) released from the gas-releasing porous substance which may be used in the present invention is not limited, but is, for example, 0.5 to 100 mL, preferably 0.5 to 50 mL, per 1 g of the porous substance.

Water or the liquid diluent which can release gas on contact with the gas-releasing substance is not limited, so long as it is suitable for oral ingestion. Liquid diluents include, for example, aqueous diluents and oily diluents. As aqueous diluents, there may be mentioned, for example, milk, soft drinks, or alcohol-containing drinks. As the oily diluents, there may be mentioned, for example, edible oils.

When releasing gas (particularly air) on contact with the water or liquid diluent, the gas-releasing substance preferably absorbs the contacting water or liquid diluent at the same time. An amount of the water or liquid diluent to be absorbed by the gas-releasing porous substance which may be used in the present invention is not limited, but is, for example, 0.1 to 5 mL, preferably 0.1 to 2 mL, per 1 g of the porous substance.

The gas-releasing substance is not limited, so long as it is a substance which may be used for oral ingestion. As the gas-releasing substance, there may be mentioned, for example, medicaments, functional foods, or foods. As the medicaments, there may be mentioned, for example, adsorbents for internal use.

As the adsorbents for internal use, there may be mentioned, for example, carbons which may be used as medicaments, active carbons, spherical carbonaceous adsorbents, oxides or hydroxides of aluminum, iron, titanium, silicon or the like, or hydroxyapatite. Spherical carbonaceous adsorbents disclosed in, for example, patent reference 4 or patent reference 5 described above are preferable. The spherical carbonaceous adsorbents disclosed in patent reference 4 are porous spherical carbonaceous substances having a diameter of 0.05 to 1 mm, a volume of pores having a pore radius of 80 angstrom or less of 0.2 to 1.0 mL/g, and having both acidic groups and basic groups.

With respect to the acidic groups and basic groups contained in the spherical carbonaceous adsorbent, a total amount of acidic groups (A) is preferably 0.30 to 1.20 meq/g, a total amount of basic groups (B) is preferably 0.20 to 0.70 meq/g, and a ratio of (A) to (B) (i.e., A/B) is preferably 0.40 to 2.5. The amount of acidic groups (A) and the amount of basic groups (B) can be determined by the following conventional methods, as described in patent reference 4 or patent reference 5.

(i) Total Amount of Acidic Groups (A)

The total amount of acidic groups is an amount of NaOH consumed, which may be determined by adding 1 g of a spherical adsorbing carbon, after being crushed to form particles having a size of less than 200 mesh, to 50 mL of a 0.05N NaOH solution; shaking the mixture for 48 hours; then filtering out the spherical adsorbing carbon; and titrating until neutralization.

(ii) Total Amount of Basic Groups (B)

The total amount of basic groups is an amount of HCl consumed, which may be determined by adding 1 g of a spherical activated carbon after being crushed to form particles having a size of less than 200 mesh, to 50 mL of a 0.05N HCl solution; shaking the mixture for 24 hours; then filtering out the spherical activated carbon; and titrating until neutralization.

In the present invention, as the adsorbents for internal use, a spherical activated carbon having a small average particle diameter disclosed in Japanese Patent Application No. 2005-108062, i.e., a spherical activated carbon having an average particle diameter of 50 to 200 µm and a specific surface area determined by a BET method of 700 $m^2/g$ or more; or a surface-modified spherical activated carbon having a small average particle diameter disclosed in Japanese Patent Application No. 2005-108063, i.e., a modified spherical activated carbon having an average particle diameter of 50 to 200 µm, a specific surface area determined by a BET method of 700 $m^2/g$ or more, a total amount of acidic groups of 0.30 to 1.20 meq/g, and a total amount of basic groups of 0.20 to 0.9 meq/g; may be used.

The amount of gas (particularly air) released from the spherical carbonaceous adsorbent by soak with water may be determined, for example, by using an apparatus shown in FIG. 1 in accordance with the following method.

A predetermined amount of the spherical carbonaceous adsorbent 7 is added to a side arm flask 6, and kept at 25° C. The mouth of the flask is sealed with a rubber plug 5 capable of preventing a leakage of air, and the flask is placed in a water tank 4 kept at 25° C. A predetermined amount of water W is charged into a cylinder 2 having a needle 3. The needle 3 is introduced through the rubber plug 5, and the water W is injected into the flask 6 by pushing on the piston 1. The amount of water W injected is to be sufficient for wetting the spherical carbonaceous adsorbent. Gas generated in the flask 6 is captured, via the side arm 8 and a tube 9, in a graduated cylinder 10 by an under water displacement method. The amount of captured air is determined from gradations of the graduated cylinder. As a control test, the same procedure is repeated, except that the spherical carbonaceous adsorbent 7 is not added to the flask 6, and the result is compensated with an amount of air captured in the graduated cylinder 10.

The amount of water adsorbed when the spherical carbonaceous adsorbent is brought into contact with water may be determined, for example, in accordance with the following method.

An excess of water is added to a predetermined amount of the spherical carbonaceous adsorbent (for example, 10 mL of water per 1 g of the spherical carbonaceous adsorbent). The mixture is stirred well so that a sufficient amount of water is absorbed by the spherical carbonaceous adsorbent. The remaining water is filtered, and an amount of water collected in a graduated cylinder or the like is measured. The difference determined between the amount of water to be added first and an amount of water to be collected is an amount of water to be absorbed. The measured value is compensated with a value obtained by a control test.

The gel base used in the composition of the present invention is not limited, so long as it is a gel-forming high molecular weight compound capable of gelatinizing the whole of the dry composition for oral ingestion of the present invention by adding water or the liquid diluent thereto.

As the gel bases which may be used in the present invention, there may be mentioned, for example, natural high molecular weight compounds (for example, polysaccharides, peptides, rubbers, or natural resins) or derivatives thereof, or synthetic high molecular weight compounds. More particularly, there may be mentioned, for example, alginate or salts thereof, propylene glycol alginate, acacia gum, carageenan, xanthan gum, guar gum, locust bean gum, tamarind gum, pectin, tragacanth, gelatin, agar, sodium starch glycolate, cellulose derivatives [for example, carmellose or salts thereof, hydroxyethylcellulose, low substituted hydroxypropylcellulose, hydroxypropylmethylcellulose (particularly, hydroxypropylmethylcellulose 2910), or methylcellulose], carboxyvinyl polymers, polyacrylates (for example, sodium polyacrylate), povidone, or dextran. These gel bases may be used alone or as a combination of two or more compounds.

When a spherical adsorbing carbon is used as the gas-releasing substance, cellulose derivatives, carboxyvinyl polymers, carmellose or salts thereof (for example, sodium carmellose), carboxymethyl starch or salts thereof (for example, sodium carboxymethyl starch), alginate or salts thereof (for example, sodium alginate), alginate derivatives (for example, propylene glycol alginate), a starch, xanthan gum, guar gum, carageenan, acacia gum, locust bean gum, tara gum, karaya gum, or tragacanth gum are preferable as the gel base. The cellulose derivatives include, for example, methylcellulose, hydroxypropylmethylcellulose, hydroxyethylcellulose, or hydroxypropylcellulose.

A weight average molecular weight of the gel base is preferably 10,000 or more, more preferably 30,000 or more. When a spherical adsorbing carbon is used as the gel-releasing substance, a gel base having a weight average molecular weight of less than 10,000 is not preferable, because such a gel base sometimes reduces an adsorbability of the spherical adsorbing carbon. The form of the gel base is not limited, so long as the gel base does not affect the dry form of the dry composition for oral ingestion. The gel base may be mixed with the gas-releasing substance in a form of, for example, powders or granules. It is preferable that a mixture of a granular gas-releasing substance and a powdery gel base is wrapped in, for example, a stick-type sachet formed from a laminated film containing aluminum foil, because the powdery gel base also functions as a lubricant.

In addition to the gas-releasing substance and the gel base, the dry composition for oral ingestion of the present invention may further contain one or more additives for formulation, if desired. As the additives, there may be mentioned, for example, sweeteners, tasting agents, perfumes, coloring agents, acidulants, reagents for masking bitterness, or other materials for formulation.

The term "dry" in the dry composition for oral ingestion of the present invention as used herein means that a substantial amount of water or a liquid diluent is not contained in the dry composition. The recitation "a substantial amount of water or a liquid diluent is not contained" means that water and/or a liquid diluent is not contained, for example, in an amount capable of promoting gelatinization of the gel base or degradation of the gas-releasing substance when the dry composition for oral ingestion is stored. More particularly, an amount of water contained therein is preferably 15% or less by weight, more preferably 10% or less by weight.

The dry composition for oral ingestion of the present invention contains the gel base in an amount of preferably 0.1 to 100 parts by weight, more preferably 0.1 to 50 parts by weight, with respect to 100 parts by weight of the gas-releasing substance (particularly a spherical adsorbing carbon). When an amount of the gel base is more than 100 parts by weight with respect to 100 parts by weight of the gas-releasing substance (particularly a spherical adsorbing carbon), a sufficient gas is not released when adding water and/or a liquid diluent, and thus, glob of gel base are sometimes generated. When an amount of the gel base is less than 0.1 parts by weight, a gel is not formed.

The dry composition for oral ingestion of the present invention may be provided in various forms.

For example, before taking immediately, one component containing the gas-releasing substance and another component containing the gel base, which are supplied to a patient in a divided form, may be added to an appropriate vessel; water and/or a liquid diluent may be added to the mixture to convert it into a gel composition for oral ingestion; and the obtained gel composition may be administered to the patient.

Further, the dry composition for oral ingestion of the present invention may be formulated in a form of a mixture of a granular or powdery gas-releasing substance (particularly a spherical adsorbing carbon) and a granular or powdery gel base. In this case, the dry composition for oral ingestion of the present invention may be prepared by mixing both. Furthermore, the dry composition for oral ingestion of the present invention may be formulated as, for example, powders, fine granules, granules, or tablets, by adding fillers (for example, starch or lactose), binders (for example, hydroxypropylcellulose or povidone), disintegrating agents (for example, carmellose calcium), and/or lubricants (for example, magnesium stearate) to the gas-releasing substance (particularly a spherical adsorbing carbon) and the gel base. In this case, conventional methods may be used for the formulation. Other additives, such as surfactants, solubilizing agents, buffers, and/or preservatives may be further added, if desired.

The dry composition for oral ingestion of the present invention may be orally administered while maintaining the dry state, but it is preferable to convert the dry composition into a gel composition for oral ingestion by adding water and/or a liquid diluent thereto immediately before oral ingestion. An amount of the water and/or liquid diluent to be added depends on the type or amount of the gas-releasing substance and the gel base contained in the composition for oral ingestion. For example, when the composition for oral ingestion contains 100 parts by weight of a spherical activated carbon and 0.5 to 10 parts by weight of xanthan gum as the gel base, it is preferable that the water or liquid diluent is contained in an amount of 100 to 2000 parts by weight with respect to 100 parts by weight of the dry composition for oral ingestion.

The term "gel" as used herein means that one semisolid aggregate as a whole is formed by adding water and/or a liquid diluent to the dry composition for oral ingestion. More particularly, the dry composition for oral ingestion is put into a flat-bottomed tube having an internal diameter of 13 mm, and mixed with water and/or a liquid diluent to form a semisolid, with stirring slightly if necessary, and the tube is inverted. After 1 minute from the inversion, a state in which the fall of the aggregate is less than 2 cm is preferable as the gel.

In general, a person who will ingest the composition of the present invention puts the dry composition for oral ingestion of the present invention into a vessel such as a cup, and adds an appropriate amount of water or a liquid diluent into the vessel, immediately before ingestion. When microbubbles are released from the gas-releasing substance and gelation is caused by the gel base, the water or liquid diluent is absorbed into the gas-releasing substance, and the gelation is promoted. As a result, a gel composition suitable for oral ingestion is formed at room temperature in an extremely short time without heating and/or cooling. The obtained gel composition for oral ingestion is formed as one gel aggregate as the whole, and does not tend to become attached to the internal sidewalls of the vessel, and thus, can be easily removed from the vessel with a spoon or the like.

A viscosity of the gel composition for oral ingestion of the present invention is preferably, for example, 0.1 Pa·S to 10,000 Pa·S, according to the measurement using a B type viscometer. The dry composition for oral ingestion of the present invention may be filled into a vessel to be used as a vessel for dividedly packaging the composition and forming a gel.

The gas-releasing substance may be easily administered to an animal other than a human by mixing a feed with the gel composition for oral ingestion of the present invention. The term "animal other than a human" as used herein means, for example, pet animals, domestic animals, or animals bred in a zoo, and includes large animals and small animals. As the large animals, there may be mentioned, for example, cattle, horses, donkeys, sheep, pigs, or goats. As the small animals, there may be mentioned, for example, cats, dogs, rabbits, guinea pigs, hamsters, ferrets, rats, or mice.

As a feed which may be mixed with the gel composition for oral ingestion, common feeds (preferably solid feeds) for the above animals may be used. Solid feeds include, for example, hay or concentrated feeds for large animals, or dried foods for small animals. A mixed feed may be obtained by preparing the gel composition for oral ingestion from the dry composition for oral ingestion, and mixing the obtained gel composition with a feed. The mixing ratio is not limited, but the gel composition for oral ingestion may be used in an amount of preferably 0.01 to 1000 parts by weight, more preferably 0.05 to 200 parts by weight, with respect to 100 parts by weight of the feed.

EXAMPLES

The present invention now will be further illustrated by, but is by no means limited to, the following Examples.
Preparative and Referential Example 1: Preparation of Porous Spherical Carbonaceous Substance A porous spherical carbonaceous substance was prepared in accordance with a method described in Example 1 of patent reference 5, and used as a gas-releasing substance.

More particularly, petroleum pitch (68 kg) (softening point=210° C.; quinoline insoluble contents=not more than 1% by weight; ratio of hydrogen atoms/carbon atoms=0.63) and naphthalene (32 kg) were charged into an autoclave (internal volume=300) equipped with stirring fans, melted at 180° C., and mixed. The mixture was extruded at 80 to 90° C. to form string-like shaped products. Then, the string-like shaped products were broken so that a ratio of a length to a diameter became about 1 to 2.

The resulting broken products were added to an aqueous solution containing 0.23% by weight of polyvinyl alcohol (saponification value=88%) and heated to 93° C., and dispersed with stirring to be spheroidized. Then, the whole was cooled by replacing the polyvinyl alcohol aqueous solution with water, at 20° C. for 3 hours, whereby the pitch was solidified and naphthalene crystals were precipitated, and a slurry of spherical shaped products of pitch was obtained.

After most of the water was removed by filtration, the naphthalene in pitch was extracted and removed with n-hexane at an amount of about 6 times that of the spherical shaped products of pitch. The resulting porous spherical pitch was heated to 235° C. by passing a heated air in a fluidized bed, and allowed to stand at 235° C. for 1hour to be thereby oxidized, and a porous spherical oxidized pitch was obtained, which is non-fusible to heat.

Thereafter, the resulting porous spherical oxidized pitch was activated in a fluidized bed at 900° C. for 170 minutes by a nitrogen gas atmosphere containing 50% by volume of steam to obtain a spherical activated carbon. Further, the resulting spherical activated carbon was oxidized in a fluidized bed at 470° C. for 3 hours and 15 minutes by a nitrogen-oxygen atmosphere containing 18.5% by volume of oxygen, and reduced in a fluidized bed at 900° C. for 17 minutes by a nitrogen gas atmosphere, to obtain a porous spherical carbonaceous substance.

Example 1

Preparation of Composition for Oral Ingestion

Gel bases shown in Table 1 were ground with a vibration ball mill to obtain powdery materials, and each powdery material (200 mg) was mixed with the porous spherical carbonaceous substance (2 g) obtained in the above Preparative and Referential Example 1. Each mixture was put into a flat-bottomed tube (internal diameter=13 mm; height=150 mm), mixed with water (10 mL), and allowed to stand for 1 minute. The flat-bottomed tube was inverted and further allowed to stand for 1 minute, and the gelatinization of each observed. The results are shown in Table 1.

TABLE 1

| Gel-forming high molecular weight compounds | Appearance |
| --- | --- |
| xanthan gum | Completely gelatinized |
| guar gum | Almost completely gelatinized |
| carageenan | Completely gelatinized |
| acacia gum | Completely gelatinized |
| locust bean gum | Completely gelatinized |
| tara gum | Almost completely gelatinized |
| carmellose sodium | Partially gelatinized |
| sodium alginate | Partially gelatinized |
| propylene glycol alginate | Completely gelatinized |
| carboxyvinyl polymer | Almost completely gelatinized |
| hydroxypropylmethylcellulose | Almost completely gelatinized |
| methylcellulose | Almost completely gelatinized |
| hydroxyethylcellulose | Completely gelatinized |
| low substituted hydroxypropylcellulose | Completely gelatinized |
| sodium carboxymethyl starch | Completely gelatinized |
| α starch | Completely gelatinized |
| karaya gum | Completely gelatinized |
| tragacanth | Completely gelatinized |

In Table 1, "Completely gelatinized" means that the fall of the resulting aggregate was less than 1 cm; "Almost completely gelatinized" means that the fall thereof was 1 to cm; and "Partially gelatinized" means that a highly mobile portion (i.e., a liquid portion) and a portion lacking in mobility (i.e., a gel portion) were observed and the fall of the liquid portion was more than 2 cm.

Example 2

Preparation of Composition for Oral Ingestion

The procedure described in Example 1 was repeated, except that each powdery material (20 mg) derived from each gel base was mixed with the porous spherical carbonaceous substance (2 g), to obtain mixtures thereof. Each mixture was put into a flat-bottomed tube, mixed with water (10 mL), and allowed to stand for 1 minute. The flat-bottomed tube was inverted and further allowed to stand for 1 minute, and the gelatinization of each observed. The results are shown in Table 2.

TABLE 2

| Gel-forming high molecular weight compounds | Appearance |
| --- | --- |
| xanthan gum | Completely gelatinized |
| guar gum | Completely gelatinized |
| carageenan | Gelatinized but soft |
| *acacia* gum | Not gelatinized |
| locust bean gum | Not gelatinized |
| tara gum | Completely gelatinized |
| carmellose sodium | Not gelatinized |
| sodium alginate | Gelatinized but soft |
| propylene glycol alginate | Not gelatinized |
| carboxyvinyl polymer | Completely gelatinized |
| hydroxypropylmethylcellulose | Completely gelatinized |
| methylcellulose | Completely gelatinized |
| hydroxyethylcellulose | Not gelatinized |
| low substituted hydroxypropylcellulose | Not gelatinized |
| sodium carboxymethyl starch | Not gelatinized |
| α starch | Gelatinized but soft |
| karaya gum | Gelatinized but soft |
| tragacanth | Gelatinized but soft |

In Table 2, "Completely gelatinized" means that the fall of the resulting aggregate was less than 1 cm; "Gelatinized but soft" means that the resulting gel aggregate was deformed by the self weight, but the fall of the aggregate was less than 2 cm, or the gel aggregate fell off the walls of the tube; and "Not gelatinized" means that the fall of the product was 2 cm or more and an apparent gel aggregate was not observed.

Comparative Example 1

The procedure described in Example 1 was repeated, except that crystalline cellulose particles (CELPHERE 305; Asahi Kasei Corporation; average particle diameter=400 μm) 2 g) were used instead of the porous spherical carbonaceous substance prepared in Preparative and Referential Example 1, and that each gel base (200 mg) shown in Table 3 was used, to obtain each mixture of the crystalline cellulose particles and each gel base. Each mixture was put into a flat-bottomed tube, mixed with water (10 mL), and allowed to stand for 1 minute. The flat-bottomed tube was inverted and further allowed to stand for 1 minute, and the gelatinization of each observed. The results are shown in Table 3. In this connection, the crystalline cellulose particles do not release gas by soak with water.

TABLE 3

| Gel-forming high molecular weight compounds | Appearance |
| --- | --- |
| xanthan gum | Gelatinized but glob of gel base was formed |
| | Not uniformalized without stirring |
| guar gum | Gelatinized but glob of gel base was formed |
| | Not uniformalized without stirring |
| tara gum | Not gelatinized |
| carboxyvinyl polymer | Became soft gel |
| | Not uniformalized without stirring |
| hydroxypropylmethylcellulose | Not gelatinized |
| methylcellulose | Not gelatinized |
| hydroxyethylcellulose | Not gelatinized |
| low substituted hydroxypropylcellulose | Not gelatinized |
| sodium carboxymethyl starch | Not gelatinized |

In Table 3, "Gelatinized but glob of gel base was formed" means that a gel product containing a macroscopically transparent portion and a microscopically opaque portion was obtained; "Not uniformalized without stirring" means that the product was uniformalized by stirring the mixture with a spoon ten or more times; "Became soft gel" means that a soft aggregate, in which a portion ran down when the aggregate was spooned up, was formed; and "Not gelatinized" means that the fall of the product was 2 cm or more and an apparent gel aggregate was not observed.

Test for Ingestion (1) Ingestion Test Example 1

A dried food for cats (product name=Sheba Duo, Umi no megumi, tuna & cheese; country of origin=Canada; importer=Master Foods, Ltd.) (two packages containing 20 g/package) was transferred to a bowl, stirred with a spoon for 2 minutes, and fed to a cat (Persian cat, castrated male, 8-year-old, body weight=7 kg) at 9:00 a.m. After 8 hours from the feeding, no dried food remained and it was all eaten.

(2) Ingestion Test Example 2

The porous spherical carbonaceous adsorbent (0.4 g) prepared in Preparative and Referential Example 1 was added to a bowl, and then, a dried food for cats (product name=Sheba Duo, Umi no megumi, tuna & cheese; country of origin=Canada; importer=Master Foods, Ltd.) (two packages containing 20 g/package) was added to the bowl. The whole was stirred with a spoon for 2 minutes, and fed to a cat (Persian cat, castrated male, 8-year-old, body weight=7 kg) at 9:00 a.m. After 8 hours from the feeding, some of the dried food was still remained. The remainder was transferred to a sieve (opening=500 μm), and the amounts of the oversize and the undersize were measured. The amount of the oversize corresponding to the dried food was 4 g, and the amount of the undersize corresponding to the porous spherical carbonaceous adsorbent was 0.3 g. Although 90% of the dried food was ingested, only 25% of the porous spherical carbonaceous adsorbent was ingested, and 75% thereof was not ingested.

(3) Ingestion Test Example 3

The porous spherical carbonaceous adsorbent (0.4 g) prepared in Preparative and Referential Example 1 and a xanthan gum (0.1 g) were added to a bowl. Tap water (approximately 4 mL) was added to the bowl to form a jelly. Further, a dried food for cats (product name=Sheba Duo, Umi no megumi, tuna & cheese; country of origin=Canada; importer=Master Foods, Ltd.) (two packages containing 20 g/package) was added to the bowl. The whole was stirred with a spoon for 2 minutes, and fed to a cat (Persian cat, castrated male, 8-year-old, body weight=7 kg) at 9:00 a.m. After 8 hours from the feeding, no dried food and the porous spherical carbonaceous adsorbent remained and it was all eaten. The porous spherical carbonaceous adsorbent was completely ingested.

Industrial Applicability

The dry composition for oral ingestion of the present invention can be converted to a gel (or a jelly) at room temperature in a very short time, at most, approximately one minute, only by mixing water or a liquid diluent therewith when taking, without heating or cooling. The obtained gel composition can be easily taken by even a person having a difficulty when swallowing.

Although the present invention has been described with reference to specific embodiments, various changes and modifications obvious to those skilled in the art are possible without departing from the scope of the appended claims.

The invention claimed is:

1. A dry composition in a granular or powdery form for oral ingestion, comprising a dry mixture comprising spherical adsorbing carbon in a granular or powdery form as an active ingredient, and a gel base in a granular or powdery form in an amount sufficient for gel formation, wherein a gelation or gelatinization of the gel base has not been promoted, said gel base being one or more substances selected from the group consisting of acacia gum, propylene glycol alginate, α starch, carageenan, karaya gum, carboxyvinyl polymers, sodium carboxymethyl starch, xanthan gum, guar gum, cellulose derivatives and salts thereof, tara gum, tragacanth, and locust bean gum;

wherein said spherical adsorbing carbon in dry granular or dry powdery form and said gel base in a dry granular or dry powdery form remain as separate ingredients in the mixture.

2. The dry composition according to claim 1, wherein the gel base is a gel-forming high molecular weight compound with a molecular weight of 10,000 or more.

3. The dry composition according to claim 1, wherein an amount of the gel base is 0.1 to 100 parts by weight with respect to 100 parts by weight of the spherical adsorbing carbon.

4. A dry composition in a granular or powdery form for oral ingestion, comprising a dry mixture comprising spherical adsorbing carbon in a granular or powdery form as an active ingredient, and a gel base in a granular or powdery form in an amount sufficient for gel formation, wherein a gelation or gelatinization of the gel base has not been promoted, said gel base being one or more substances selected from the group consisting of acacia gum, propylene glycol alginate, α starch, carageenan, karaya gum, carboxyvinyl polymers, sodium carboxymethyl starch, xanthan gum, guar gum, cellulose derivatives and salts thereof, tara gum, tragacanth, and locust bean gum;

wherein said dry mixture is prepared by a process consisting essentially of mixing said spherical adsorbing carbon in dry granular or dry powdery form with said gel base in a dry granular or dry powdery form, wherein said dry composition is not in the form of a gel or a wherein said spherical adsorbing carbon in dry granular or dry powdery form and said gel base in a dry granular or dry powdery form remain as separate ingredients in the mixture table.

5. The dry composition according to claim 4, wherein the gel base is a gel-forming high molecular weight compound with a molecular weight of 10,000 or more.

6. The dry composition according to claim 4, wherein an amount of the gel base is 0.1 to 100 parts by weight with respect to 100 parts by weight of the spherical adsorbing carbon.

* * * * *